(12) United States Patent
Iwasaki et al.

(10) Patent No.: US 10,058,651 B1
(45) Date of Patent: Aug. 28, 2018

(54) SAFETY NEEDLE DEVICE FOR ACCESSING A MEDICAL PORT

(71) Applicant: Suntori Medical, LLC, Denver, CO (US)

(72) Inventors: Dean H. Iwasaki, Denver, CO (US); James V. Mercer, West Jordan, UT (US); Thomas L. Taccini, Denver, CO (US)

( * ) Notice: Subject to any disclaimer, the term of this patent is extended or adjusted under 35 U.S.C. 154(b) by 424 days.

(21) Appl. No.: 14/693,647

(22) Filed: Apr. 22, 2015

Related U.S. Application Data

(60) Provisional application No. 61/995,844, filed on Apr. 22, 2014.

(51) Int. Cl.
 A61M 5/162 (2006.01)
 A61M 5/158 (2006.01)
 A61M 25/06 (2006.01)
 A61B 5/15 (2006.01)

(52) U.S. Cl.
 CPC ..... *A61M 5/1626* (2013.01); *A61B 5/150664* (2013.01); *A61B 5/150671* (2013.01); *A61B 5/150679* (2013.01); *A61B 5/150687* (2013.01); *A61M 5/158* (2013.01); *A61M 25/06* (2013.01); *A61M 25/0612* (2013.01); *A61M 25/0618* (2013.01); *A61M 25/0631* (2013.01); *A61M 2005/1581* (2013.01); *A61M 2005/1583* (2013.01); *A61M 2005/1585* (2013.01)

(58) Field of Classification Search
 CPC .............. A61M 25/0631; A61M 25/06; A61M 25/0612; A61M 25/0618; A61M 5/1626; A61M 5/158; A61M 2005/1583; A61M 2005/1581; A61M 2005/1585; A61B 5/150664; A61B 5/150671; A61B 5/150679; A61B 5/150687
 See application file for complete search history.

(56) References Cited

U.S. PATENT DOCUMENTS

| | | | | |
|---|---|---|---|---|
| 2004/0049159 | A1* | 3/2004 | Barrus | A61M 5/158 604/174 |
| 2005/0049553 | A1* | 3/2005 | Triplett | A61M 5/158 604/110 |
| 2009/0163875 | A1* | 6/2009 | Hiraoka | A61M 5/158 604/192 |

* cited by examiner

*Primary Examiner* — Nathan R. Price
*Assistant Examiner* — Anh Bui

(57) ABSTRACT

A Safety Huber needle assembly comprising a needle used to pierce the septum of an implanted venous port, a baseplate that rests against the insertion site and a pivotally displaceable housing that acts to remove the needle from the septum of the implanted port and to effectively enclose the needle to provide user safety when the housing is displaced to a needle securing state.

16 Claims, 4 Drawing Sheets

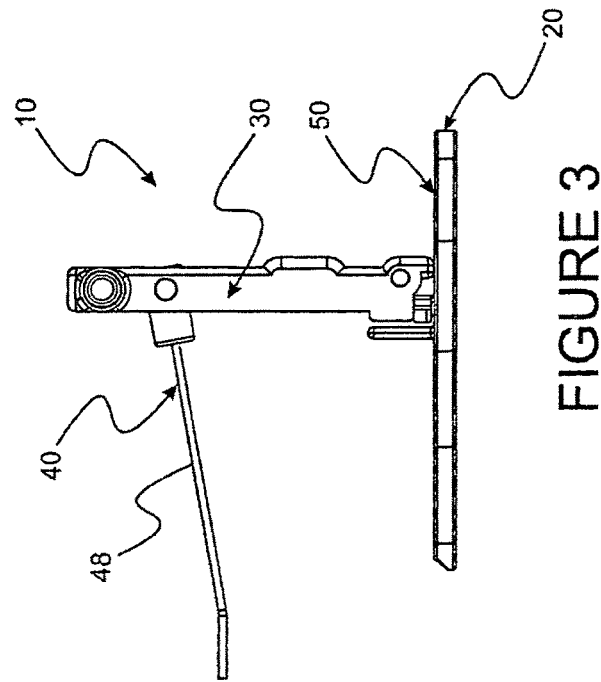
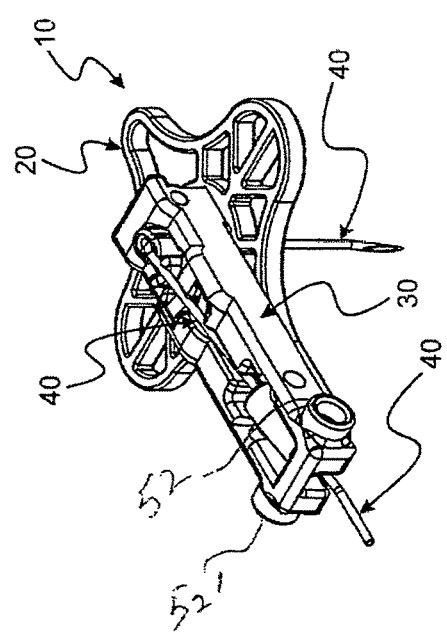
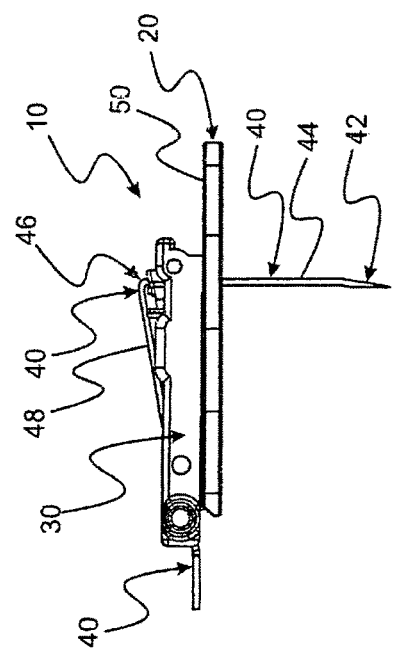

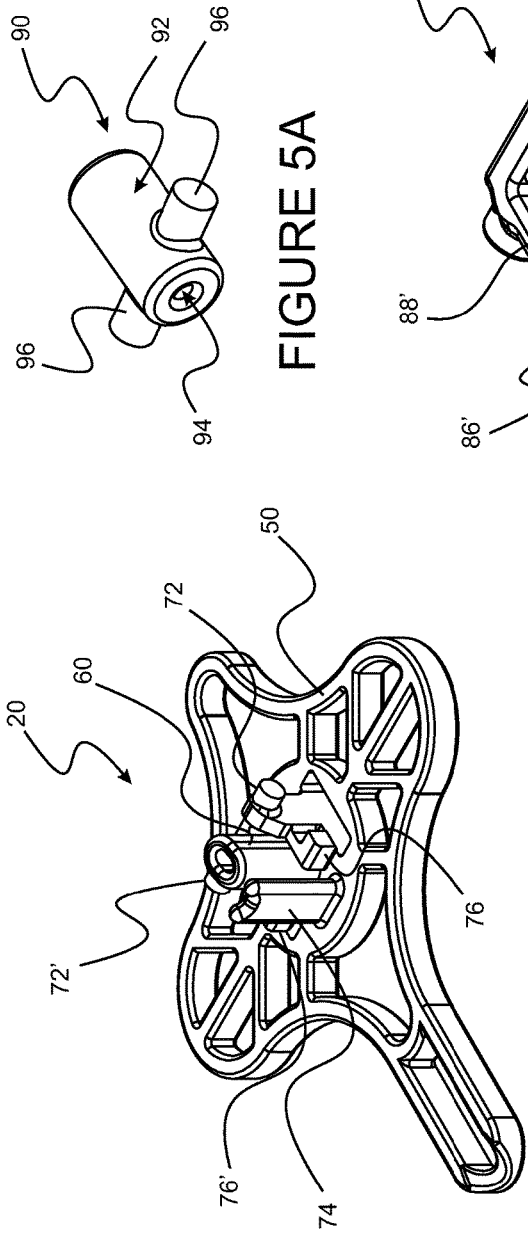
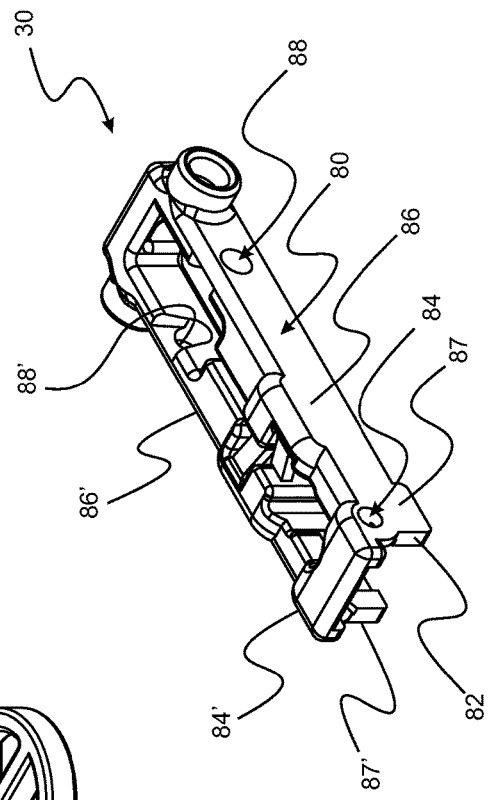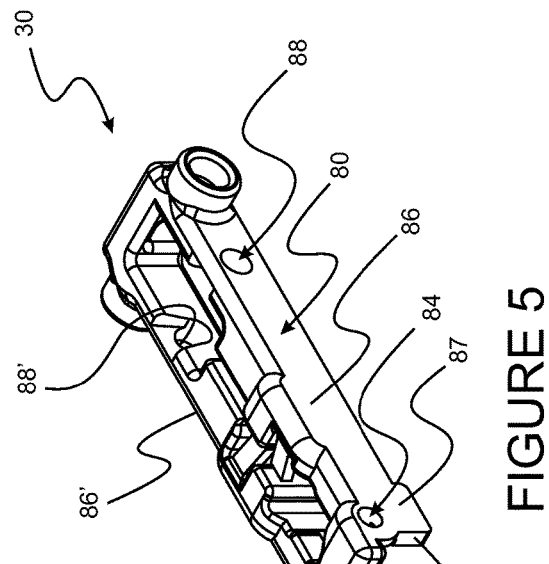

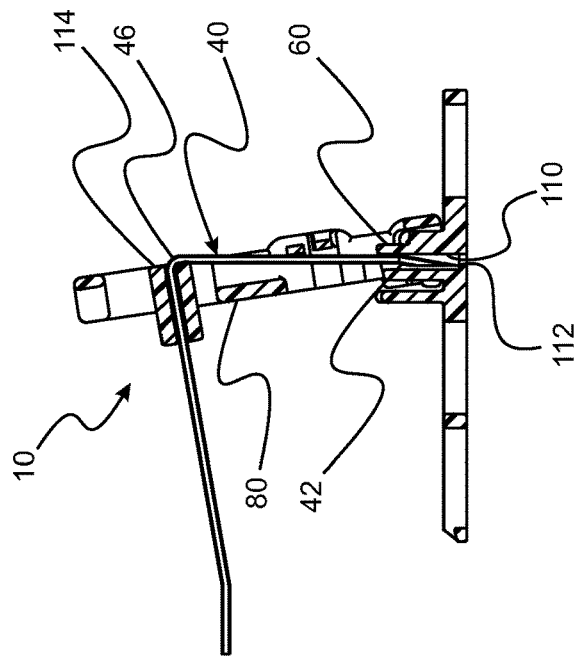
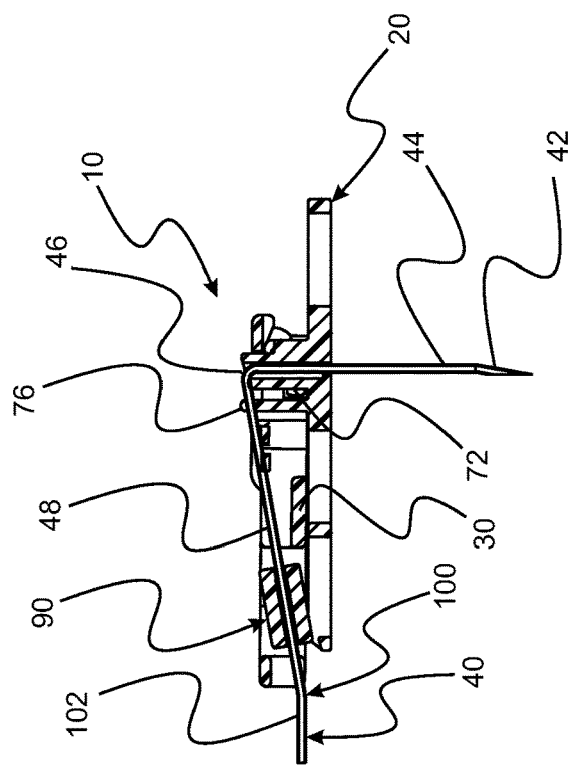

SAFETY NEEDLE DEVICE FOR ACCESSING A MEDICAL PORT

CROSS-REFERENCE TO RELATED APPLICATIONS

This application claims the benefit of and priority to U.S. Provisional Patent Application No. 61/995,844, filed Apr. 22, 2014, the entire contents of which are incorporated by reference herein.

FIELD OF THE INVENTION

This invention generally relates to devices which penetrate implanted venous access ports for administering intravenous chemotherapy, intravenous nutrition (TPN), intravenous fluids, intravenous blood and blood products as well as other intravenous solutions commonly used in healthcare.

BACKGROUND AND DESCRIPTION OF RELATED ART

Implanted venous access ports generally have a self-sealing septum through which a preferably non-coring needle pierces. The septum seals around the non-coring needle being inserted into such an implanted venous access port to ensure that intravenous solution, being administered, does not leak into surrounding tissues. The instant invention is designed to provide protection to healthcare workers and patients from an inadvertent and potentially fatal encounter with a sharpened, blood or other bodily fluid covered tip of a needle when being retracted from the implanted venous port, as well as during disposal post-removal. Further, the instant invention preferably employs a non-coring needle for further patient protection. Examples of U.S. Patents which Applicants consider to be relevant, but do not teach or suggest devices or methods associated with the instant invention are provided hereafter:

U.S. Pat. No. 6,322,537 issued Nov. 27, 2001, to Joseph J. Chang and titled SAFETY INTRAVENOUS CATHETER discloses a medical IV catheter which comprises a needle cannula having distal point, a proximal end and further having a shaft with a circumference and a tip protector which is slideably mounted on the needle. In FIG. 1, the needle is taught to be protected by a short tip protector device which is limited in movement by a bulging portion of the needle. In another embodiment, the needle is drawn proximally to a catch also associated with a bulge on the needle. In both cases, the needle is linear in form.

U.S. Pat. No. 6,355,021 issued Mar. 12, 2002 to Jan Willum Nielson, et al. and titled MEDICAL PUNCTURING DEVICE discloses a medical puncturing device comprising a rigid needle being at one end adapted for facilitating the puncturing and comprising at the opposite end a hub, the hub comprising a handle part and a shield which is pivotal in relation to the handle part and further comprising a locking means on the shield and handle. A straight puncturing needle is retracted from an inserted catheter through a self-sealing septum and then bent into a safety cavity to ensure an unintended harmful injury is avoided. In particular, this device is used to insert a catheter into a patient fluid pathway.

U.S. Pat. No. 6,659,983 issued Dec. 9, 2003 to Jamieson William Maclena Cawford, et al. and titled NEEDLE ASSEMBLY discloses an automatically shieldable blood collection set. The set includes a needle assembly having a hub to which a needle cannula is fixedly attached. The needle hub includes a fin formed with a latch. A safety shield is telescoped relative to the hub and the needle cannula is moved from a proximal position where the needle cannula is exposed to a distal position where the cannula is shielded. The latch on the fin releasably engages the shield when the shield is in the proximal position. A spring is provided between the shield and hub to propel the shield distally relative to the hub and into surrounding relationship with the needle cannula in response to movement of the latch. FIGS. 1 and 2 show the action of the shield is a straight path, with the shield being actuated by a spring being advance to provide protection about the needle tip.

U.S. Pat. No. 6,878,136 (136) issued Apr. 12, 2005 to Michael T. Fleury, et al. and titled HUBER NEEDLE WITH ANTI-REBOUND SAFETY MECHANISM discloses a safety needle device for a huber needle. The device includes a needle housing having a distal housing opening, an arcuate groove extends within the needle housing terminating adjacent a distal housing opening. The needle is disclosed to have an arcuate shape, seen best in FIG. 7A. A shield disposed about the needle (see FIG. 3) is advanced (see FIGS. 1 and 2) to provide a shield for the needle tip.

Table of Term Definitions

Baseplate n; a generally planar, rigid member used as an interface at an insertion site, the baseplate is often fitted with planar side extensions for applying digital pressure to maintain device stability during needle insertion. A baseplate according to the instant invention also comprises an aperture through which a vertically disposed needle is displace, means for hingeably affixing a needle housing thereto, tabs for locking a needle housing in place and an elongated orifice pathway provided by a hollow vertical cylindrical column used as a needle guide and needle tip enclosure.

Cam n; a part of a housing which comprises a rotatable hollow cylindrical portion disposed about an associated needle. The cylindrical portion rotating as the associated housing is displaced from a first state to a second state to provide orthogonal lift force upon a needle which disposed within the cylindrical portion and to thereby displace the needle from engagement at an access port.

Essentially adv; close enough in form and function to meets the needs of a modified term though not necessarily meeting the exact criteria of the so modified term Housing n; a member which acts as a needle guide and enclosure for a portion of an insertable needle, the housing being rotationally affixed to the baseplate such that in a first rotational state, the needle is exposed for insertion into an access port and in a second rotational state, which is orthogonal to the baseplate, provides an enclosure for a portion of a segment of the needle which was inserted into the access port.

Lip Edge n; a sub-component of the baseplate, located at the base of the inner bore of the vertical cylindrical column to provide a surface for the tip of the needle to rest upon, once retracted, thereby preventing the needle from being displaced downward and outward from the baseplate through the aperture.

Locking Tab n; a sub-component of the baseplate, disposed at a pre-determined location near the vertical cylindrical column for interacting with a complementary component on the housing to thereby engage and render a locked structure which inhibits displacement of the housing relative to the baseplate when the housing is pivoted to a second upright state.

Needle n; a cannula having a sharpened tip, generally used for penetration of a biological access port, a needle according to the instant invention having a series of sequential bends to provide a segment with the tip for penetrating an access site, a segment for interfacing with the cam for displacing the needle from the access site and a segment for connecting to fluid communicating tubing.

Pivot Post n; a post which is a sub-component of the baseplate, located at a pre-determined location around the vertical cylindrical column and affixed thereat to act as a point of attachment for rotatably coupling the baseplate to the housing.

Vertical Cylindrical Column n; a sub-component of the baseplate disposed on the top surface of the baseplate, hollowed to encompass a baseplate aperture and extended vertically to provide an enclosing pathway through which the vertical segment of an accessing needle passes.

Vertical Support Structure n; a sub-component of the baseplate, located on the top surface of the baseplate, to the rear of the vertical cylindrical column for supporting the needle during the first housing state (i.e. state of housing during needle insertion).

BRIEF DESCRIPTION AND OBJECTS OF THE INVENTION

The instant invention provides a novel safety device for inserting a needle with a sharpened end tip into a patient access site and for removing the needle into a safety enclosure and locking the needle thereat to fully enclose the needle tip, thereby ensuring against an inadvertent needle stick.

The invention comprises a baseplate which is used to stabilize the inventive device against skin at an insertion site, to provide a pivot interface for a housing and to provide a needle guide and trap about a pathway along which the needle is vertically displaced when retracting the needle from an insertion site. Pivotally affixed to the baseplate is an elongated body of the housing which is displaced relative to the baseplate from an initial state parallel to the baseplate to a second state which is essentially orthogonal to the baseplate whereby the needle is retracted. At an end of the body away from the baseplate/housing affixing site, a rotatable cam, with a centrally disposed hollow cylindrical pathway, is affixed to longitudinally rotate thereat. A needle, preferably with a non-coring sharpened tip, comprising a series of bends is disposed to provide (1) a vertical section defining an insertion pathway for the needle, (2) a non-vertical section which provides a pathway for the cam to be displaced along the needle as the housing is angularly displaced to the second state, the cam thereby providing force to lift and draw the needle vertically from the insertion site, the baseplate and housing thereafter providing a safety enclosure for the needle and needle tip. Upon pivoting the housing to the second state, the housing is locked in place thereat with latches disposed at the surface of the baseplate and the needle is also locked and enclosed within the housing and baseplate to guard against inadvertent contact and needle sticks.

With such, the needle is inserted into an access site with the housing in the first state for use in a medical procedure. Following completion of the procedure, the housing is pivoted to an orthogonal disposition relative to the baseplate to vertically withdraw the needle from the access site and into safety of enclosure within baseplate and housing. Note, that withdrawal of the needle requires only simple rotation of the housing. Latches are provided as parts of the baseplate and the housing to lock the housing in the orthogonal or second state and secure the needle in place.

An exemplary embodiment of the present invention comprises a needle assembly which includes a non-coring needle, a baseplate, a housing with a sliding cam and a commercially available extension set affixed to the rear of the non-coring needle. The needle preferably has a smooth exterior and internal lumen of consistent size. The insertable end of the needle is a solid, tapered tip designed to pierce both the skin and the septum of the implanted port without coring. The outflow path of the internal lumen is toward the rear of the insertable portion of the needle, immediately superior to a solid, tapered tip. The upper body of the needle has three linear segments positioned at predetermined locations along the length of the needle interrupted by two bends, providing a segment for needle insertion, a segment disposed along a pathway of the rotating cam and a tubular connecting segment for fluid communication therewith. Of course, adding a non-coring feature to the needle also adds a third needle bend.

The baseplate has two safety mechanisms comprising (1) a surface to surface lock which interacts with the housing and (2) a trap which captures a retracted needle tip upon being retracted from the septum of the implanted venous port. Note, that the baseplate supports the non-coring needle both in the vertical and horizontal planes. In the vertical plane, the needle is supported within a needle vertical support column which retards lateral motion during insertion and keeps the needle vertical during retraction. As the housing is rotated to the second state, the rotating cam acts upon the associated needle segment to lift the insertion segment of the needle vertically (orthogonally relative to the plane of the baseplate). Note also that, the needle is supported within the assembly by a vertical support structure within the baseplate. The vertical support structure encloses the sharpened tip when the housing is in the second state.

It is therefore a primary object to provide a safety needle port accessing device by which a needle is inserted into a port with a housing in a first state and by which the needle is displaced orthogonal to a skin contacting baseplate to be retracted into a safety enclosure by a single motion involving a simple rotation of the housing to a second state.

It is another object to provide a housing which is locked from rotation relative to a baseplate in the second state to assure the needle is kept fully enclosed for safety.

It is an important object to provide a device which withdraws an inserted needle along a line which is the line of needle insertion.

In a preferred embodiment, it is an object to employ a non-coring needle to guard against generating particulates during an accessing process.

These and other objects and features of the present invention will be apparent from the detailed description taken with reference to accompanying drawings.

BRIEF DESCRIPTION OF THE DRAWINGS

FIG. 1 is a perspective of a device made according to the instant invention with a housing disposed in a first state relative to an associated baseplate.

FIG. 2 is a side elevation of the perspective of the device seen in FIG. 1.

FIG. 3 is a side elevation of the device seen in FIG. 2 with the housing angularly displaced relative to the baseplate.

FIG. 4 is a perspective of the baseplate seen in FIG. 1.

FIG. 5 is a perspective of the housing seen in FIG. 1.

FIG. 6 is a cross section of the device seen in FIG. 1.

FIG. 5A is a perspective of a cam part which, when disposed in a housing, rotates while sliding along a needle.

FIG. 7 is a cross section of the device seen in FIG. 1 with the housing angularly displaced to a second state.

DETAILED DESCRIPTION OF THE ILLUSTRATED EMBODIMENTS

Figure 8:
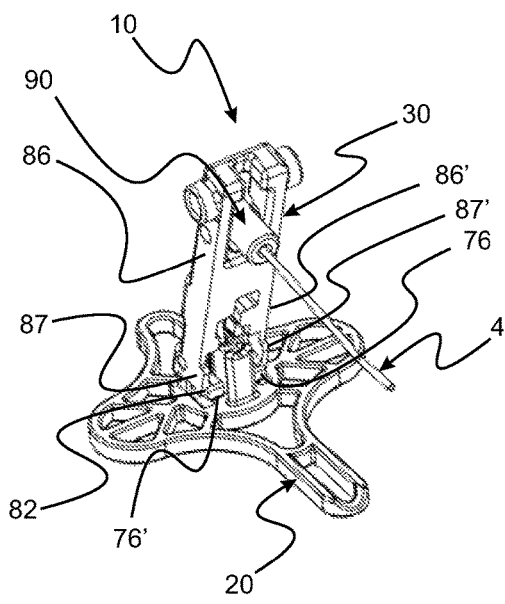
FIG. 8 is a perspective of the device seen in FIG. 7 to be pivoted toward a second state, but before locking tabs are engaged.

In this description, the term proximal is used to indicate the segment of a device normally closest to the object of a sentence describing its position. The term distal refers to the other end. Reference is now made to FIG. 1-9 wherein the same numbers are used to designate like parts throughout. Parts which are similar in function and construction, but which are not identical, are referenced by primes of numbers. Reference is now made to FIG. 1 wherein a safety needle assembly 10 made according the instant invention is seen. Assembly 10 comprises a baseplate 20, a housing 30 and a medical needle 40. Parts associated with baseplate 20 and housing 30 are preferably injection molded from sturdy biologically inactive synthetic resinous material such as polypropylene or polycarbonate. Needle 40 is preferably made, as is well known in the medical needle art, from stainless steel.

A side elevation of assembly 10 in FIG. 2 illustrates needle 40 having a non-coring sharpened tip 42. Needle 40 is disposed with a segment 44, which is continuous with tip 42, bared and vertical for insertion into an access site. More distal from tip 42 and segment 44 of needle 40 is a bend at feature 46 to form a non-vertical segment 48. In the state of assembly 10 in FIG. 2, housing 30 is disposed parallel to a top surface 50 of baseplate 20. Such a state is defined as the first state of housing 30 or the "ready for insertion of needle 40" condition of assembly 10.

In FIG. 3, housing 30 is pivoted to a second state which is an essentially orthogonal relationship with surface 50. Such pivoting of housing 30 results in needle tip 42 and associated segment 44 (not seen in FIG. 3) being vertically displaced into a safety enclosure provided in combination by baseplate 20 and housing 30, as is disclosed in more detail hereafter. Pivoting housing 30 relative to baseplate 20 is facilitated by a pair of gripping posts (numbered 52 and 52'), both seen in FIG. 1, which provide digital contacts for easy rotation when grasped and displaced to reposition housing 30 from the first state to the second state.

Baseplate 20 is seen in FIG. 4 to comprise a hollow vertical cylindrical column rising from surface 50. Structure 70, comprising a pair of outwardly extending pivot posts (numbered 72 and 72') are disposed for snap-in pivotal attachment of complementary features on housing 30. A vertical stabilizing interface 74 Provides stable support for needle 40 while housing 30 is disposed in the first state. A pair of latching arms (each numbered 76 and 76') is provided to catch upon complementary parts of housing 30 to secure housing 30 after being pivoted to the second state.

Housing 30 is seen in FIG. 5 to comprise a body 80 without an associated cam 90 (see FIG. 5A) affixed thereto. Body 80 is elongated a length which corresponds with the length of segment 48 of needle 40 (see FIG. 2). At one end 82, body 80 comprises a pair of opposing bore-through holes 84 and 84' (hole 84' is not seen in FIG. 5) in side walls 86 and 86', respectively. Body 80 also comprises a pair of tabs 87 and 87' inferiorly disposed at end 82. Function and purpose for tabs 87 and 87' are fully addressed relative to FIGS. 8 and 8A. Bore holes 84' and 84 are sized and located to provide a snap-in connection with posts 72 and 72', respectively, of baseplate 20 (see FIG. 4). So disposed, posts 72 and 72' provide an axis of rotation for housing 30 relative to baseplate 20.

A second pair of opposing bore holes (numbered 88 and 88') are disposed in sidewalls 86 and 86', respectively, of body 80. Reference is now made to FIG. 5A wherein a cam 90 is seen. Cam 90 comprises an elongated cylindrical body 92, a bore through hole 94 and a pair of cylindrical arms (commonly numbered 96). Arms 96 are sized and dimensioned to snap into holes 88 and 88' in body 80 (see FIG. 5) to rotatably affix cam 90 to body 80 and complete assembly of housing 30.

In FIG. 6, assembly 10 is seen fully assembled with segment 44 and tip 42 distending from baseplate 20. Note that segment 48 subtends an acute angle relative to segment 44. Preferably, the subtended angle is 80 degrees. Cam 90 is rotationally displaced to accommodate segment 48 as it extends distally from bend 46. Distal to segment 48, needle 40 comprises a second bend 100 which provides an upwardly directed segment 102 whereat a medical fluid communicating set can be affixed. The upward direction of segment 102 relieves a connected set from uncomfortable contact at an insertion site.

As also seen in FIG. 6, segment 48 is not restrained within device 10 from a small vertical displacement away from a needle 40 insertion site relative to baseplate 20. This small vertical displacement provides for a variation in depth of penetration of needle 40 by acting to provide a method for reducing a potential gap which may occur between patient skin surface and baseplate 20. For, when baseplate 20 is displaced downward towards the site (as when segment 44 of a needle 40 cannot be fully inserted), cam 90 rotates permissively to allow segment 48 of a needle 40 to slide therein and, thereby, to permit baseplate 20 to be displaced toward and against the insertion site for increased device 10 stability.

With cam 90 and segment 48 disposed as seen in FIG. 6, any upward rotational displacement of housing 30 results in a vertical displacement of needle 40, the greatest leverage for vertical displacement occurring as housing 30 is initially displaced from the first state. By sliding along segment 48 and rotating during housing 30 displacement, cam 90 converts pivoting action of housing 30 into vertical displacement of needle 40 which is critical in retraction of a needle from an access site as is well known in medical art.

Assembly 10 with a fully retracted needle 40 is seen in FIG. 7. Note that the combined length of body 80 and length of the internal hollow core 110 of vertical cylindrical column 60 fully enclose segment 44 and tip 42 of needle 40. Note further that vertical cylindrical column 60 comprises a lip edge 112 against which tip 42 is captured and retained. Also note that cam 90 is comprises a leading edge 114 whish is disposed against needle 40 at bend 46 to further constrain needle 40.

Figure 8A:
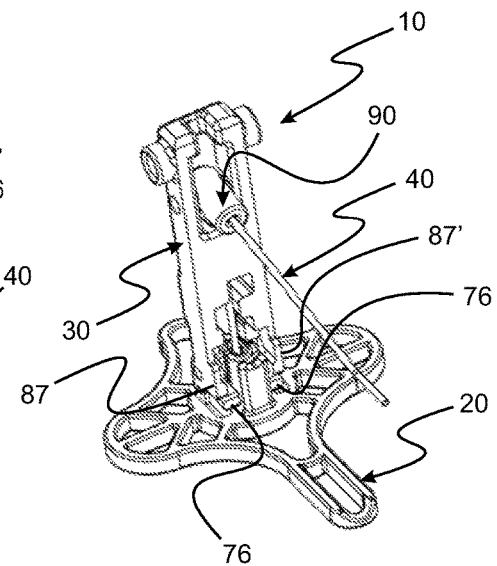
FIG. 8A is a perspective of the device seen in FIG. 8 with locking tabs engaged.
Figure 9:
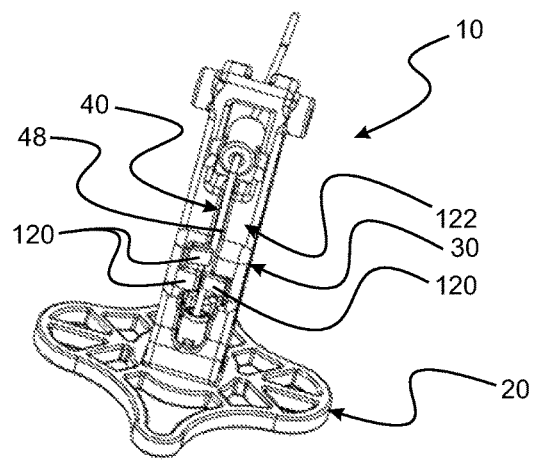
FIG. 9 is a perspective of the device seen in FIG. 8 with needle locking tabs engaged.

Latching of housing 30 relative to baseplate 20 is best seen in FIGS. 8 and 8A. As housing 30 nears the second state, as seen in FIG. 8, latches 76 and 76' are relieved from engaged disposition by inner surfaces of tabs 87' and 87, respectively. In FIG. 8A housing is fully pivoted to the second state and latching arms 76 and 76' are engaged against tabs 87 and 87', respectively to lock housing 30 in the second state.

Also for safety, housing 30 comprises a plurality of tabs (generally numbered 120 which are disposed along the top side 122 of housing 30. Tabs 120 are sized and disposed to catch upon segment 48 of needle 40 as housing 30 is seated in the second state. Thereby, another safety process is provided to inhibit unintended needle 40 displacement thereafter.

The invention may be embodied in other specific forms without departing from the spirit or essential characteristics thereof. The present embodiment is therefore to be considered in all respects illustrative and not restrictive, the scope of the invention being indicated by the appended claims rather than by the foregoing description, and all changes which come within the meaning and range of equivalency of the claims are therefore intended to be embraced therein.

What is claimed is:

1. A safety needle assembly for use in accessing an implanted venous infusion port comprising:
   a. a baseplate component which provides a stable interface for said safety needle assembly at a port access site;
   b. a housing comprising an elongated body pivotally affixed at one end to said baseplate and comprising a pair of gripping posts disposed on the other end, said housing being displaceable to two stable states comprising a first state in which said body is disposed parallel to said baseplate from which said body is displaced by application of digital force upon gripping posts of said body to pivot said body to a second state wherein said body is essentially orthogonal to said baseplate;
   c. a cam which is swivelly affixed to said housing, said cam comprising an orifice through which a segment of a needle is disposed, said cam and said orifice rotating to provide vertical displacement of the needle assembly, a portion of which slides within said orifice, as said housing is displaced from the first state to the second state; and
   d. the needle assembly comprising a first vertically disposed segment and a second segment residing in said orifice, said first segment being displaced to penetrate and access a port when the housing is disposed in a first state and being retracted from the access site to be enclosed for safety when the housing is displaced to the second state by action of said cam against said orifice residing segment.

2. A safety needle assembly according to claim 1 wherein said needle is a non-coring needle.

3. A safety needle assembly according to claim 1 wherein said baseplate and said housing comprise tabs and stops to thereby, in combination, provide a secured safety housing for said first segment of said needle assembly when the housing is in the second state.

4. A safety needle assembly for use in accessing an implanted venous infusion port comprising:
   a. a baseplate comprising an aperture through which a needle can freely pass;
   b. a housing comprising an elongated body and which is rotatably affixed to said baseplate, said housing comprising a fixture for the retention of a rotating cam, said housing further comprising hinged connecting structure whereby the housing is affixed to the baseplate for being angularly displaceable between a first state where the elongated portion is parallel with the baseplate and a second state where the elongated body is essentially orthogonal to the baseplate baseplate and gripping posts whereby the housing is digitally displaced from the first state to the second state;
   c. the cam comprising a hollow channel there-thru and two side projections which fit into the housing to provide an axis about which said cam pivots when said housing is rotated to the second state, said channel providing a pathway by which a segment of a needle is displaced
   d. a needle subassembly comprising an elongated cannula having a sharpened, tapered tip, a lumen of consistent size there-thru and an outflow orifice and being bent to form a plurality of segments comprising a vertical segment which ends at said tip, a non-vertical segment bent at an angle consistent with displacement via arcuate motion of said cam and a connecting segment for communicating with an extension set;
   e. an extension set affixed at the connecting segment of the needle assembly.

5. A safety needle assembly according to claim 4 wherein said baseplate further comprises a hollow vertical cylindrical column surrounding said aperture which extends vertically for a predetermined distance, the primary purposes of said cylindrical column being providing a stabilizing structure for said needle during needle insertion and for enclosing at tip of the needle after retraction from an infusion port.

6. A safety needle assembly according to claim 5 wherein said baseplate further comprises two pivot posts disposed about the aperture and a vertical cylindrical column for providing pivot posts which act to attach between the baseplate to the housing and provide an axis of rotation for the housing relative to the baseplate.

7. A safety needle assembly according to claim 5 wherein said baseplate further comprises a vertical support structure distal to the vertical cylindrical column for supporting the housing during needle access at an insertion site.

8. A safety needle assembly according to claim 5 wherein said baseplate further comprises two locking tabs disposed at the base of the vertical cylindrical column, said locking tabs comprising displaceable structure which is thrust aside by housing displacement toward the second state but allowed to return to a latching disposition when the housing is disposed in an essentially vertical position, thereby providing a safety enclosure for said needle and needle tip.

9. A safety needle assembly according to claim 5 wherein said baseplate further comprises a lip edge disposed on the inferior end of the inner wall of the vertical cylindrical column providing a barrier for the needle tip when the housing is displaced to the second state.

10. A safety needle assembly according to claim 4 wherein said fixture of said housing further comprises a plurality of recessed channels disposed along sides of the body of the housing, said channels comprising chamfered lead-ins and holes, provided to secure the cam via pivot posts for angular displacement of the cam relative to the body.

11. A safety needle assembly according to claim 4 wherein said body of said housing further comprises tabs for interacting with the baseplate to prevent said housing from rotating more than 90 degrees from the first state.

12. A safety needle assembly according to claim 8 wherein said body of said housing further comprises two planar tabs designed to accommodate and cover without engaging the two baseplate locking tabs, said body further comprising chamfered protrusions within said planar tabs for acting upon said baseplate locking tabs, to force said tabs inward as the housing is being displaced to the second state such that when said chamfered protrusions extend past said planar tabs, the protrusions return to their initial state and, thereby, lock said housing in the second state.

13. A safety needle assembly according to claim 8 wherein said body of said housing further comprises at least one secondary needle locking tab which engages the needle when the primary housing is displaced to its vertical position, each of said at least one secondary needle locking tabs comprising a flexible parts which distends inwards toward a needle trough into which the vertical portion of the needle is displaced and latched when said housing is displaced to the second state.

14. A safety needle assembly according to claim 8 wherein said needle further comprises a bend angle between said vertical segment and said non-vertical segment of 80 degrees.

15. A safety needle assembly according to claim 8 wherein said needle is non-coring.

16. A safety needle assembly according to claim 8 wherein said cam is disposed in said housing such that, in combination, displacement of said housing from the first state to the second state displaces said needle from an inserted state into a safety enclosure formed by said housing in combination with said baseplate.

\* \* \* \* \*